United States Patent [19]

Goel et al.

[11] Patent Number: 4,761,479

[45] Date of Patent: Aug. 2, 1988

[54] CRYSTALLINE QUINAPRIL AND A PROCESS FOR PRODUCING THE SAME

[75] Inventors: Om P. Goel; Uldis Krolls, both of Ann Arbor, Mich.

[73] Assignee: Warner-Lambert Company, Morris Plains, N.J.

[21] Appl. No.: 32,209

[22] Filed: Mar. 30, 1987

[51] Int. Cl.$^4$ ............................................. C07D 217/16
[52] U.S. Cl. ..................................... 546/147; 544/344
[58] Field of Search ......................................... 546/147

[56] References Cited

U.S. PATENT DOCUMENTS 4,294,832 10/1981 Yoneda et al. ...................... 546/147
4,344,949 8/1982 Hoefle et al. ....................... 546/147

*Primary Examiner*—Glennon H. Hollrah
*Assistant Examiner*—James H. Turnipseed
*Attorney, Agent, or Firm*—Elizabeth M. Anderson

[57] ABSTRACT

A novel crystalline form of quinapril and a novel process for the large scale preparation of the ACE inhibitor, quinapril, in a highly pure state. The substance is of high bulk density suitable for formulation in capsules and tablets. This inexpensive process uses HCl gas in glacial acetic acid for rapid and clean de-t-butylation at room temperature.

8 Claims, No Drawings

CRYSTALLINE QUINAPRIL AND A PROCESS FOR PRODUCING THE SAME

BACKGROUND OF THE INVENTION

Quinapril is a generic term used to identify a chemical compound, 2-[2-[[1-(ethoxycarbonyl)-3-phenylpropyl]amino]-1-oxopropyl]-1,2,3,4-tetrahydro-3-isoquinoline carboxylic acid hydrochloride (S,S,S):

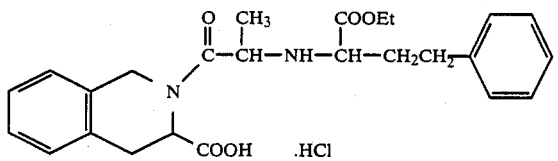

This compound and its pharmaceutically acceptable salts are active as angiotensin converting enzyme inhibitors and thus are antihypertensive agents. The compound and its use are covered in U.S. Pat. No. 4,344,949.

The compound may be prepared from 1,2,3,4,-tetrahydroisoquinoline-3-carboxylic acid by first protecting the carboxylic acid group, preferably as an ester, e.g., with a lower alkyl, of from one to four carbon atoms, benzyl or trimethylsilyl group. The protected carboxylic acid compound is coupled to an N-protected amino acid, e.g., glycine or L-alanine, protected on nitrogen with t-butyloxycarbonyl or benzyloxycarbonyl. The coupling is carried out by any of a variety of standard peptide coupling techniques as disclosed, for example, in "The Peptides. Analysis, Synthesis, Biology, Vol. 1 Major Methods of Peptide Bond Formation, Part A", ed. E. Gross, J. Meierhofer, Academic Press N.Y. (1979). An especially useful method involves the use of a dehydrating agent, such as dicyclohexylcarbodiimide alone or in the presence of reagents forming reactive esters, e.g., 1-hydroxybenzotriazole, in suitable aprotic solvents such as dimethylformamide, acetonitrile, tetrahydrofuran or chlorinated hydrocarbons. This gives the intermediate (N-protected-2-aminoacyl)-1,2,3,4-tetrahydroisoquinoline-3-carboxylic acid esters. These may then be either partially or totally deblocked depending on the protecting groups chosen, using anhydrous acids, e.g., hydrochloric acid in acetic acid or trifluoroacetic acid in methylene chloride, or hydrogen gas and a catalyst to give the intermediate dipeptide either in free form or protected as an ester.

The compound may then be prepared by reacting the intermediate dipeptide or its ester derivative with α-keto-4-substituted phenylbutyric acid or its lower alkyl ester derivatives under dehydrating and reducing conditions. Preferred dehydrating agents include molecular seives in aprotic solvents and preferred reducing agents include sodium cyanoborohydride or hydrogen gas with a catalyst.

Alternatively, the dipeptide or its ester derivative may be reacted with an α-halo-4-substituted phenylbutyric acid or its ester in the presence of a suitable basic reagent, such as triethylamine or alkali carbonates or bicarbonates, in a solvent, to give the compound. Ester protected products may be hydrolyzed under basic or acidic reaction conditions to free acid derivatives, or, in the case of benzyl esters, catalytic hydrogenolysis may be preferred.

Alternately, the compound may be prepared in a different manner. This consists of applying either of the two methods described above for the attachment of the 2-(4-phenylbutyric acid) moiety to the protected dipeptide, first to glycine or L-alanine, which may be protected as an ester, to give N-[2-(4-phenylbutyric acid)]-substituted glycine or L-alanine derivative.

After selective deblocking of the acid moiety on the glycine or alanine portion of the product, the resulting monoacid may be coupled, either directly or subsequent to suitable blocking of the amino group, via standard peptide coupling procedures to the 1,2,3,4-tetrahydro-3-isoquinoline carboxylate, protected as an ester. Selective or complete removal of the ester groups and any amine protectig groups yield the compound.

The products are obtained typically as a mixture of diastereoisomers which can be separated by standard methods of fractional crystallization or chromatography.

The compounds of this invention form acid salts with various inorganic and organic acids which are also within the scope of the invention. The pharmaceutically acceptable acid addition salts of the compounds of the present invention may be prepared by conventional reactions by reacting the free amino acid or amino ester form of the product with one or more equivalents of the appropriate acid providing the desired anion in a solvent or medium in which the salt is insoluble, or in water and removing the water by freeze drying. The salts of strong acids are preferred such as the salts of hydrochloric, hydrobromic, sulfuric, nitric, acetic, fumeric, malic, maleic and citric acids.

Large scale recrystallization of quinapril regardless of the method whereby it is produced involved the problem that the crude final products were not purifiable by conventional organic chemistry techniques. In order to obtain material of reasonable purity the crude products were dissolved in water, the insoluble gummy impurities filtered off and the products isolated by freeze drying. This proved to be expensive and time consuming.

The impurities formed during the last synthetic step are in the amounts of from 10 to 30% when either trifluoroacetic acid or HCl gas/CH$_2$Cl$_2$ are used to remove the t-butyl group from the pure t-butylester recursor. Examination of the byproducts by thin layer chromatography and NMR revealed that they are a complex of the drug, the corresponding diketopiperazine (shown below) and two other unidentified impurities. There is no starting material present.

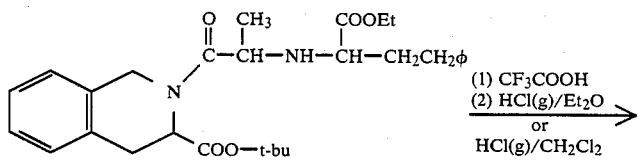

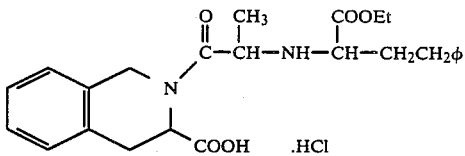

.HCl

+ by-products

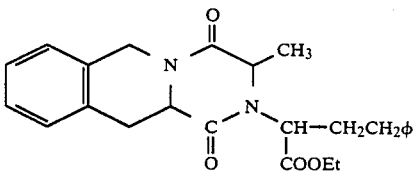

The presence of the above complex has foiled all previous attempts to purify the drug substance by recrystallization.

SUMMARY

Alternative reagents were considered for removal of the t-butyl group which would preclude the formation of diketopiperazine and produce instead the final drug substance as the hydrochloride salt in a form pure enough that simple recrystallization methods would give final purification.

The present invention provides crystalline quinapril, a novel, highly pure substance of high bulk density suitable for formulation in the desired forms such as capsules or tablets. Its properties are those sought in a pharmaceutical product. The present invention provides a process for producing crystalline quinapril. This crystalline form contains equimolar amounts acetonitrile as part of the crystalline structure.

DETAILED DESCRIPTION

The present invention provides a novel form of crystalline quinapril with the following unique X-ray diffraction properties.

| Spacing 'd' | Relative Intensities |
| --- | --- |
| 11.946 | 11 |
| 9.825 | 44 |
| 7.971 | 30 |
| 6.417 | 22 |
| 5.372 | 30 |
| 5.277 | 37 |
| 4.720 | 18 |
| 4.461 | 61 |
| 4.133 | 24 |
| 4.022 | 99 |
| 3.770 | 30 |
| 3.562 | 49 |
| 3.278 | 32 |
| 3.089 | 17 |
| 2.969 | 24 |
| 2.894 | 19 |
| 2.557 | 18 |
| 2.488 | 15. |

Crystalline quinapril has a density within the range of 0.4–0.8 g/ml. The crystals are obtained in a highly pure state. They are of high bulk density. The term density means having a density above about 0.4 g/ml. These characteristics readily lend themselves to pharmaceutical formulating operations. The solvent present in the crystal structure can be removed under vacuum (2–10 mm) and at 50°. This renders the substance amorphous as evidenced by the lack of sharp peaks in the x-ray diffraction spectrum. The high density of the product and high purity are preserved after the acetonitrile is removed.

A crystalline form is obtained by recrystallization from acetone used in a 1:1 molar ratio. Acetone, unlike acetonitrile, is however not removed if the substance is dried at 50° (2–10 mm) over periods up to seven days.

Higher temperatures are inadvisable since they lead to cyclization of the product to a diketopiperazine derivative.

The present invention also provides a process for producing crystalline quinapril which comprises:

(a) dissolving and stirring a diester of compound I above in a reagent such as HCl gas in glacial acetic acid;

(b) diluting the above mixture with xylene and stripping under vacuum to produce a solid;

(c) dissolving the solid in acetonitrile and filtering the solution;

(d) seeding the solution and cooling to room temperature;

(e) collecting and drying the product at 25 to 50° C. under vacuum for 1 to 24 hours to produce the crystalline product; and (f) further drying under vacuum at 50°–60° C. for 1–16 hours produces product free of acetonitrile.

Preferred process conditions include in step (a) HCl gas in glacial acetic acid as the reagent with a reaction time between one and six hours.

Also in step (a) the preferred diester 2-[2-[[1-Ethoxycarbonyl)-3-phenylpropyl]amino-1-oxopropyl]-1,2,3,4-tetrahydro-3-isoquinolinecarboxylic Acid, 1,1--Dimethylethyl Ester (S,S,S).

In step (c) the solid is preferably dissolved in acetonitrile at a temperature of about 25° to about 50° C.

In step (e) the drying of the product takes place at 25° to 50° C. over a time period of fourteen to eighteen hours.

The preparation of crystalline quinapril is illustrated by the following nonlimiting example.

Example I

| Chemicals | Amounts | Source |
| --- | --- | --- |
| 2-[2-[[1-Ethoxy carbonyl)-3-phenyl propyl]amino-1-oxopropyl]-1,2,3,4-tetrahydro-3-isoquinoline-carboxylic Acid, 1,1-Dimethylethyl Ester (S,S,S) | 8 g (0.016 mole) | OPG-15038x108 |
| 1.5 N HCl (g)/gl HOAc | 40.4 ml | UK 15853x129 |

A solution of the diester in glacial acetic acid containing HCl (gas) was stirred magnetically and the reaction progress followed by tlc. The reaction was complete after one hour and 20 min. After an additional hour, the reaction mixture was diluted with 70 ml of xylene and stripped under house vacuum at a bath temperature of 35° C. This step was repeated with 3×50 ml portions of xylene followed by 4×50 ml portions of n-hexane. The residue was evacuated under high vacuum to afford 9.84 of a glassy solid. The residue was dissolved in 21 ml of acetonitrile at 60° C. and the solution filtered. The pale yellow filtrate was seeded and cooled to room temperature. After cooling in the refrigerator over the weekend, the product was collected and washed with cold acetonitrile and then n-pentane. The product was dried at 50° C. under house vacuum for 16 hours to afford 7 g (91.2% yield) of a white crystalline solid, m.p. 103.5°–105° C., $[\alpha]_D^{25} + 15°$ (2% in CH$_3$OH), HPLC: 99.7% (LC-15963×19C). The NMR spectrum, however, indicated presence of acetonitrile. A second crop was isolated from the mother liquor, yield 0.18 g (2.3%), m.p. 110°–113° C.

One gram of the first crop from above was recrystallized from 15.0 ml of acetonitrile. The product was dried at 50° C. under an oil pump vacuum for 16 hours to yield 0.82 g of a white crystalline solid, free of acetonitrile, m.p. 119°–121.5° C., gas bubbles, viscous melt. The sample had the following properties:

$[\alpha]_D^{25} + 15.4°$ (2% in CH$_3$OH).

NMR (d$_6$DMSO and CDCl$_3$) V-44441, 44440: In agreement with previous spectra. I.R. (KBr and Nujol mull) MX-184980, 184981. In agreement with previous spectra.

Thin Layer Chromatography (Developer #1) Homogeneous.

HPLC #LC-15963 ×26B indicates at least 99.4% purity; no impurities were detected.

Water (K-F): 0.0%.

Solution Clarity Test: A test solution in water was clear and colorless but turned cloudy after overnight storage.

Microanalysis: Calc'd for C$_{25}$H$_{31}$N$_2$O$_5$Cl: C, 63.21; H, 6.58; N, 5.90; Cl, 7.47 Found C, 63.09; H, 6.40; N, 5.81; Cl, 7.61, 7.28.

We claim:

1. Crystalline quinapril hydrochloride exhibiting essentially the following X-ray diffraction data:

| Spacing 'd' | Relative Intensities |
|---|---|
| 11.946 | 11 |
| 9.825 | 44 |
| 7.971 | 30 |
| 6.417 | 22 |
| 5.372 | 30 |
| 5.277 | 37 |
| 4.720 | 18 |
| 4.461 | 61 |
| 4.133 | 24 |
| 4.022 | 99 |
| 3.770 | 30 |
| 3.562 | 49 |

-continued

| Spacing 'd' | Relative Intensities |
|---|---|
| 3.278 | 32 |
| 3.089 | 17 |
| 2.969 | 24 |
| 2.894 | 19 |
| 2.557 | 18 |
| 2.488 | 15. |

2. Crystalline quinapril hydrochloride according to claim 1 having a density within the range of 0.4–0.8 g/ml.

3. A process for the preparation of a compound of formula

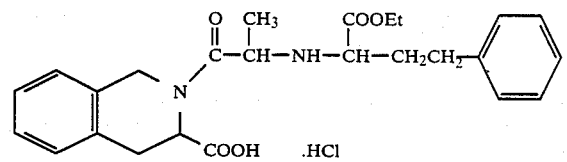

which comprises:
(a) dissolving and stirring a diester of compound I above in a reagent selected from the group consisting of HCl gas in glacial acetic acid and trifluoroacetic acid in methylene chloride,
(b) diluting the above mixture with xylene and stripping under vacuum to produce a solid,
(c) dissolving the solid in acetonitrile and filtering the solution,
(d) seeding the filtrate and cooling to room temperature, and
(e) collecting and drying the product at 25° to 50° C. under vacuum for 1 to 24 hours.

4. A process according to claim 3 wherein in step (a) the reagent is HCl gas in glacial acetic acid.

5. A process according to claim 3 wherein in step (a) the reaction runs for from one to six hours.

6. A process according to claim 3 wherein in step (a) the diester is 2-[2-[[1-Ethoxycarbonyl)-3-phenylpropyl]amino-1-oxopropyl]-1,2,3,4-tetrahydro-3-isoquinolinecarboxylic Acid, 1,1-Dimethylethyl Ester (S,S,S).

7. A process according to claim 3 wherein in step (c) the solid is dissolved in acetonitrile at from about 25° to about 50° C.

8. A process according to claim 3 wherein in Step (e) the drying under 20 to 25 mm vacuum lasts for from fourteen to eighteen hours.

* * * * *